United States Patent
Cota

[19]

[11] Patent Number: 5,922,939
[45] Date of Patent: Jul. 13, 1999

[54] HUMIDITY SENSOR

[75] Inventor: Roger Cota, Portland, Oreg.

[73] Assignee: Veris Industries, Inc., Portland, Oreg.

[21] Appl. No.: 09/137,555

[22] Filed: Aug. 20, 1998

Related U.S. Application Data

[62] Division of application No. 08/813,249, Mar. 7, 1997., Pat. No. 5,844,138

[51] Int. Cl.⁶ .......................... G01M 19/00; F16L 55/10; G01F 15/00; G01N 1/22
[52] U.S. Cl. ...................... 73/29.01; 73/31.05; 73/29.05; 73/866.5
[58] Field of Search ................ 73/29.01, 29.02, 73/29.05, 31.05, 866.5, 864.74

[56] References Cited

U.S. PATENT DOCUMENTS

| | | | |
|---|---|---|---|
| 1,100,171 | 6/1914 | Brown | 73/28 |
| 1,455,263 | 5/1923 | Oberfell | 73/23 |
| 2,412,782 | 12/1946 | Palmer . | |
| 2,663,190 | 12/1953 | Ilgenfritz . | |
| 2,852,739 | 9/1958 | Hansen | 324/61 |
| 2,943,488 | 7/1960 | Strobel et al. | 73/336.5 |
| 3,243,674 | 3/1966 | Ebert . | |
| 3,287,974 | 11/1966 | Ciemochowski . | |
| 4,001,758 | 1/1977 | Esper et al. | 338/34 |
| 4,253,336 | 3/1981 | Pietzuch | 73/422 R |
| 4,362,580 | 12/1982 | Kane et al. | 148/16 |
| 4,373,392 | 2/1983 | Nagamoto | 73/336.5 |
| 4,558,595 | 12/1985 | Kompelien | 73/336 |
| 4,660,407 | 4/1987 | Takami et al. | 73/23 |
| 5,014,908 | 5/1991 | Cox | 236/44 |
| 5,296,819 | 3/1994 | Kuroiwa et al. | 324/670 |
| 5,317,274 | 5/1994 | Nakagawa et al. | 324/678 |
| 5,385,060 | 1/1995 | Wang | 73/866.5 |
| 5,410,920 | 5/1995 | Westwick | 73/866.5 |
| 5,450,765 | 9/1995 | Stover | 73/866.5 |
| 5,612,499 | 3/1997 | Andrew et al. | 73/866.5 |
| 5,677,476 | 10/1997 | McCarthy et al. | 73/29.01 |

Primary Examiner—Hezron Williams
Assistant Examiner—J. David Wiggins
Attorney, Agent, or Firm—Chernoff, Vilhauer, McCLung & Stenzel, LLP

[57] ABSTRACT

A highly accurate relative humidity sensing device includes a sensory unit having a humidity sensitive capacitor which has a capacitance which changes as a function of relative humidity. The sensor unit is housed in a tubular unit which is inserted through an aperture into the environment to be measured which is typically a duct or the like. The unit is constructed for easy removability. A housing having a central aperture is bolted to the duct and the tube containing the sensor is inserted through the aperture into a hole drilled into the sidewall of the duct. The cylinder holding the sensor is grasped by a releasably detachable securing structure. By releasing the securing structure, the cylinder may be withdrawn from the duct for replacement of the sensor.

7 Claims, 4 Drawing Sheets

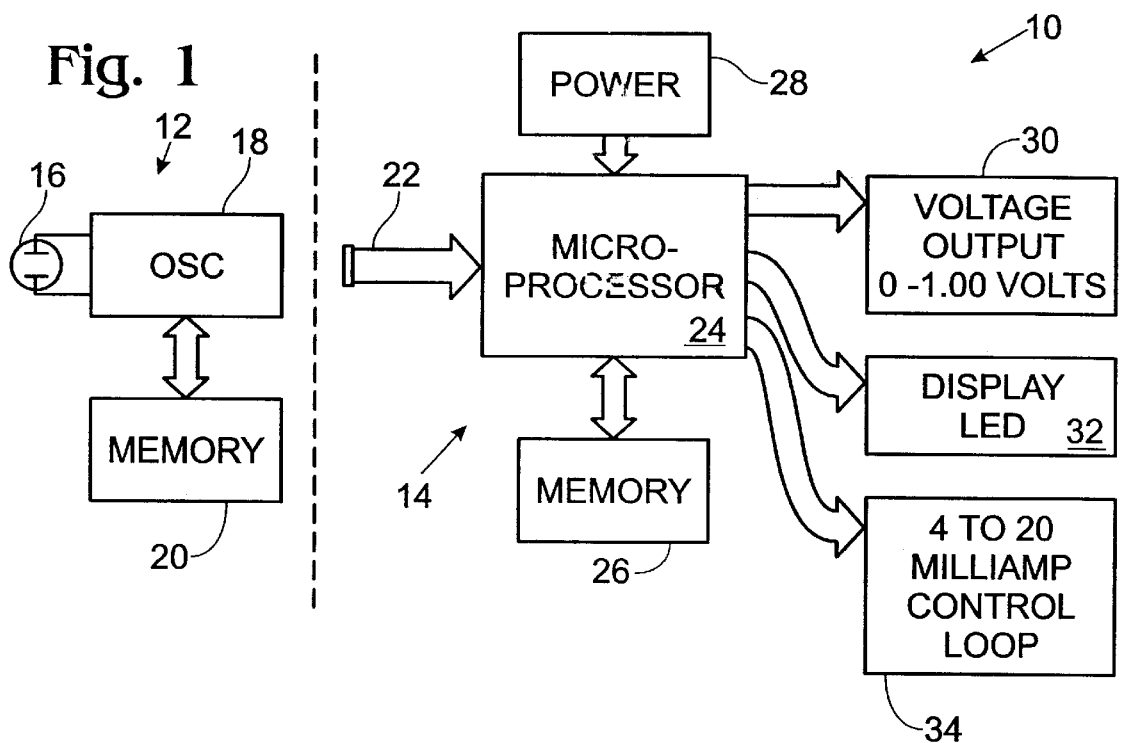
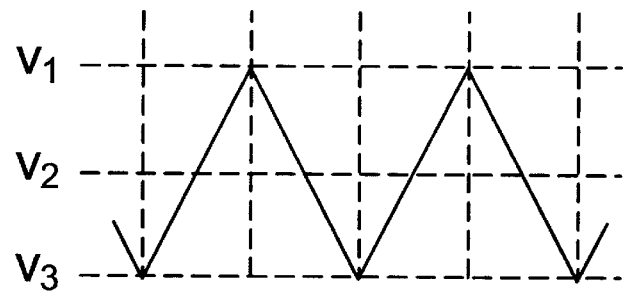
Fig. 3
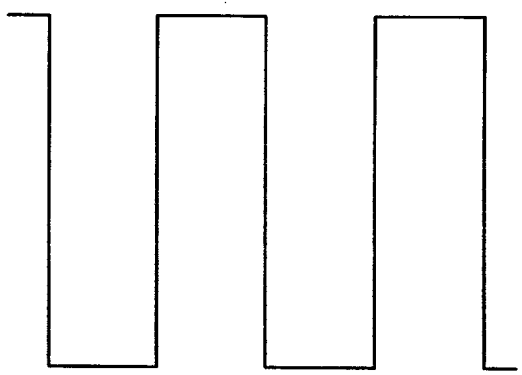

HUMIDITY SENSOR

This is a division of U.S. Ser. No. 08/813,249, now U.S. Pat. No. 5,844,138, filed on Mar. 7, 1997.

BACKGROUND OF THE INVENTION

The following invention relates to a humidity sensor and in particular to a calibrated humidity sensor for use in industrial or office heating and cooling systems.

Heating and cooling systems for climate control in large buildings such as office buildings and industrial plants not only regulate temperature relative to the ambient atmosphere, but also temperature as a function of relative humidity. In addition, humidifiers are sometimes used with such systems and it has been found that relative humidity in the range of 45–55% is the optimal comfort range. In addition, certain environments in process control must have their humidity regulated fairly precisely. Another example of an environment requiring regulation of relative humidity is a greenhouse which requires the maintenance of a high relative humidity.

The regulation of humidity and/or temperature in response to humidity is controlled by a humidity sensor. In the past, relative humidity sensors have been of two general types. Some humidity sensors use a humidity sensitive polymer on a porous ceramic plate. The resistivity of the polymer changes as a function of relative humidity. The problem with such devices is that they are not accurate enough for most applications and are also subject to chemical deterioration in harsh environments. Another type of humidity sensitive device employs a capacitor with an air dielectric. Since the dielectric constant of air is one and the dielectric constant of water is about 80, changes in the relative humidity between the capacitor plates changes the dielectric, and, hence, the capacitance of the sensor. The changes in capacitance can be used in a number of ways in circuits to provide an electrical output that is indicative of the relative humidity.

The problem with such devices is that they are sensitive and the nominal capacitance of such devices can be altered, for example, during installation. Systems that employ this type of capacitor, however, obviously depend upon the accuracy of the sensors' nominal capacitance. Nominal capacitance is also important because the slope of the curve describing capacitance versus relative humidity may differ for different capacitances. For example, small capacitors sold under the trade name MiniCap by Panametrics of Waltham, Mass. exhibit linear characteristics for changes in capacitance over a wide range of relative humidity. However, the linear slope of such capacitors differs for capacitors having different capacitances. In general, the higher the capacitance, the steeper the slope of the capacitance versus relative humidity curve. Thus, a difference in capacitance from the nominal rated capacitance of the sensor not only affects its nominal reading, but its reading at higher relative humidities. While quality control assures that capacitors leaving the factory meet nominal standards, by the time such units are assembled into sensors and installed in the field, the capacitance of such units may have changed. This leads to unacceptable errors in the measurement of relative humidity.

BRIEF SUMMARY OF THE INVENTION

A highly accurate relative humidity sensing device is provided by the present invention which includes a sensor unit having a humidity sensitive capacitor which has a capacitance which changes a function of relative humidity. The capacitor forms a part of an oscillator circuit wherein the frequency of the oscillator in the circuit is a function of the capacitance of the humidity sensitive capacitor. A sensor memory unit is included in the sensor unit which has stored within it calibration data for the humidity sensitive capacitor with which provides its true capacitance as measured against a known standard. The calibration data thus provides a memory profile of each capacitor unit that is used to correct relative humidity measurements made by the sensor unit in the environment of actual use.

The sensor unit is selectively connectable to a data processing unit which includes a data processing circuit for receiving an output of the oscillator. The data processing unit includes a data processing memory which is coupled to the sensor memory unit. The calibration data is, thus, downloaded from the sensor unit to the data processing memory unit and measurements received by the data processing circuit are modified by the calibration data to correct the aforementioned changes in capacitance.

The calibration factors are obtained by measuring the capacitance of each humidity sensitive capacitor to be included in a sensor unit against known relative humidity standards. These measurements may be made at two relative humidity points, one greater than about 70% relative humidity, and the other measurement at about less than 30% relative humidity. Since it is known that capacitance is a linear function of relative humidity, the slope of the response curve of the humidity sensitive capacitor may be determined by the two measurement points, one at the high end of the relative humidity scale and the other at the low end.

The sensor unit must be placed in an environment which undergoes temperature as well as humidity changes. It is known, however, that electrical components such as standard circuit elements may be susceptible to changes in temperature and their nominal values may drift accordingly. Thus, the sensor unit includes a voltage divider network that compensates for changes in temperature which may have an effect on the nominal values of circuit elements. The voltage divider network includes a pair of matched resistors coupled in series with a center tap therebetween. The center tap of the voltage divider network is connected to the input of an integrating amplifier which includes the sensor capacitor. The input to the voltage divider network and the output of the voltage divider network are selectively alternatively coupled by a switch to the input of the integrating amplifier and the input of a comparator amplifier whose output drives the switch. In this way any drift in components that would cause a change in the bias level on the integrating amplifier will cause a corresponding change in the threshold switching point of the comparator amplifier.

The sensor unit is housed in a tubular unit which is inserted through an aperture into the environment to be measured which is typically a duct or the like. The unit is constructed for easy removability. A housing having a central aperture is bolted to the duct and the tube containing the sensor is inserted through the aperture into a hole drilled in the sidewall of the duct. The cylinder holding the sensor is grasped by a swage nut which is tightened against the housing. Thus by loosening the swage nut the cylinder may be withdrawn from the duct for replacement of the sensor.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 1 is a block schematic diagram of the relative humidity sensing system of the invention.

FIG. 3 is a wave form diagram showing the operation of the circuit of FIG. 2.

DETAILED DESCRIPTION OF THE INVENTION

Figure 2:
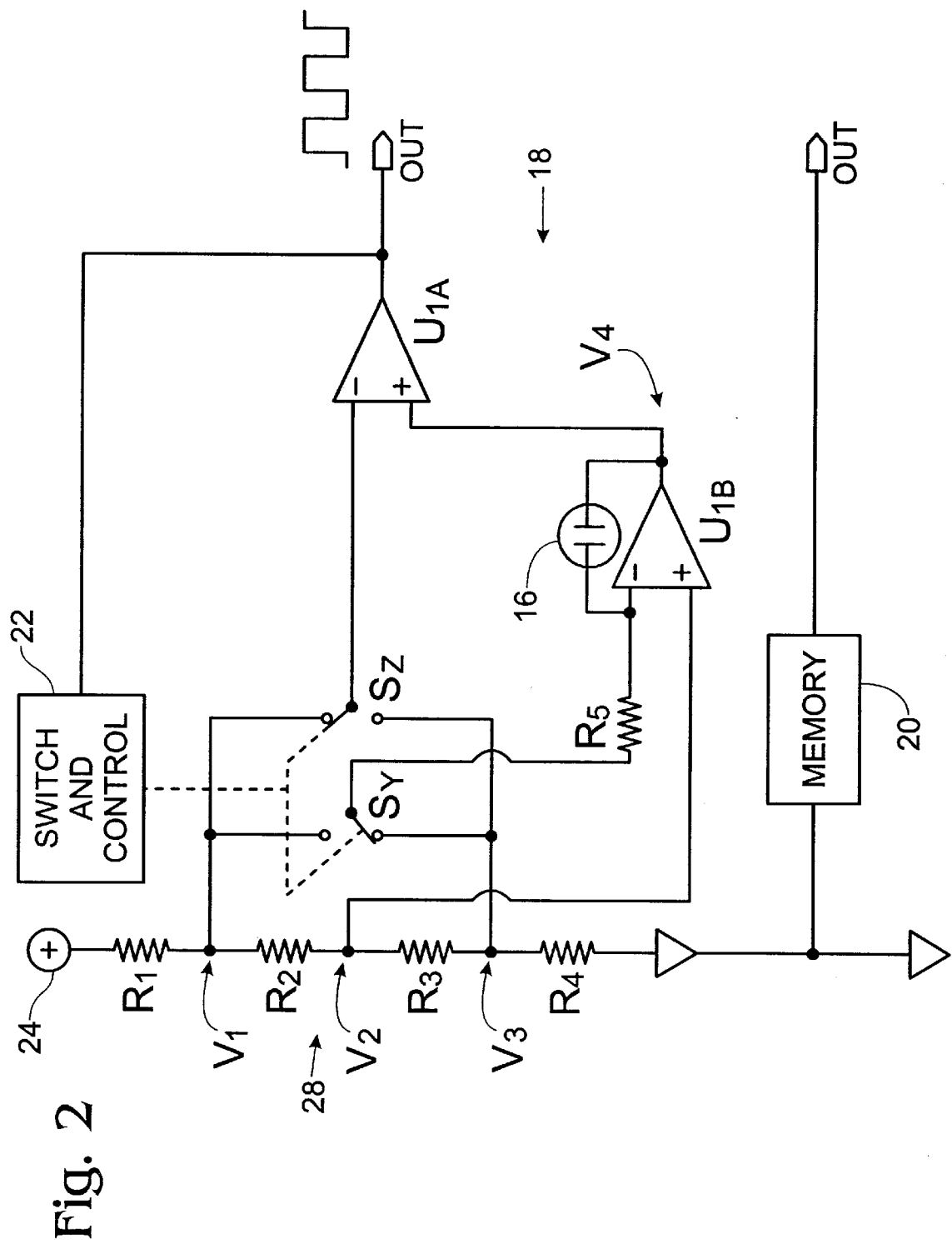
FIG. 2 is a simplified schematic diagram of the sensor electronics section of FIG. 1.

A relative humidity sensing system 10 includes a sensor unit 12 and a data processing unit 14. The sensor unit 12 may be selectively detachably connected to the data processing unit 14 because as will be explained below, each sensor unit includes a unique memory map of the relative humidity sensing capacitor 16 which is to be inserted into an environment to measure relative humidity. The sensor unit 12 includes the sensing capacitor 16, associated sensor electronics 18, and a nonvolatile memory 20.

The sensor unit 12 is connected by a bus 22 to a microprocessor 24. The microprocessor 24 includes a memory unit 26. The microprocessor 24 is powered by a power supply 28 and provides outputs which may include a voltage output from 0 to 1 volt 30, display LED 32, and a 4–20 milliamp process control loop 34.

Figure 4:
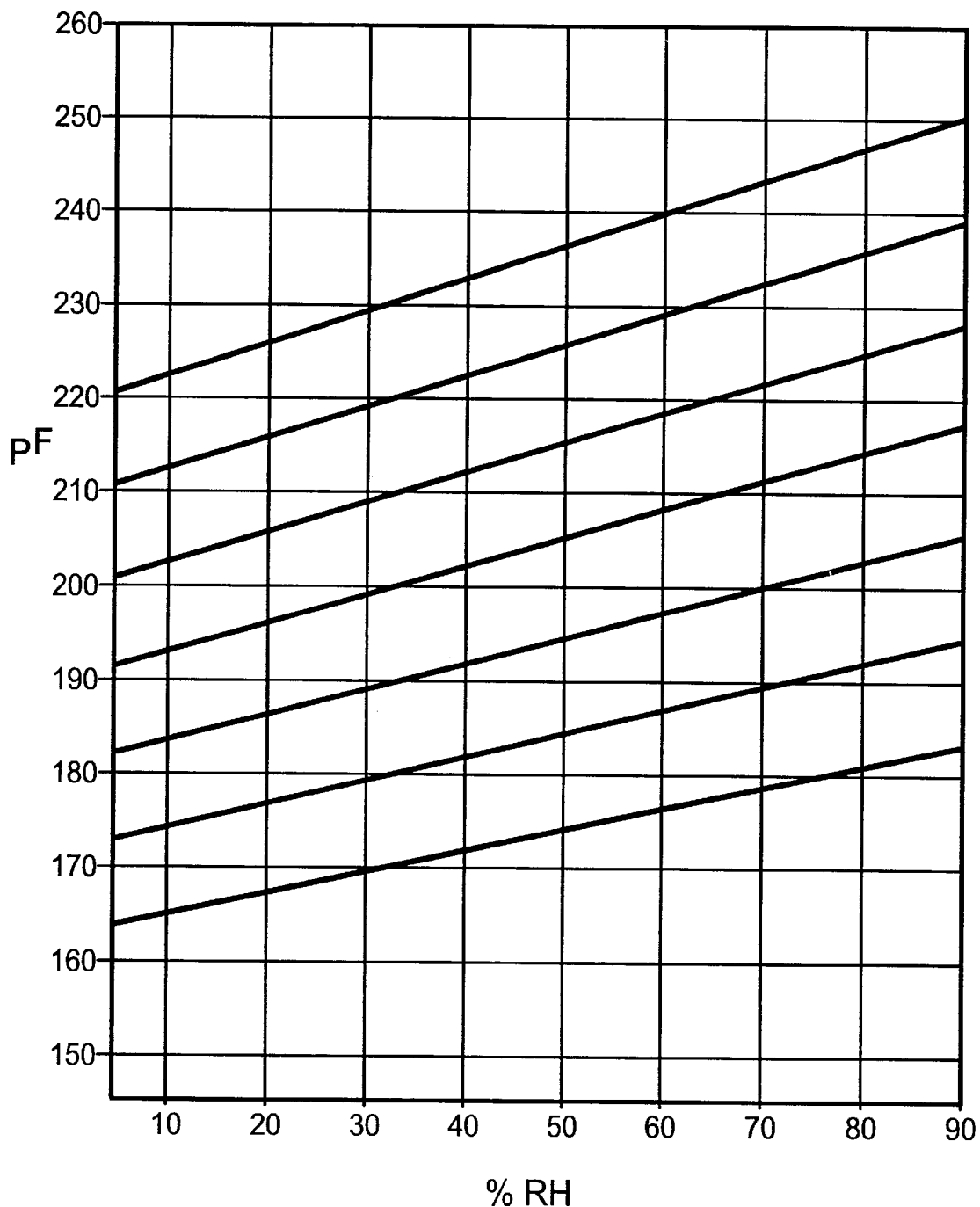
FIG. 4 is an exemplary set of curves depicting changes in capacitance of standard sensor units as a function of relative humidity.

The sensor element 16 is a commercially available sensing capacitor. The manufacturers of such devices, one being Panametrix of Waltham, Mass., publish response curves for capacitors of varying nominal capacitance. A family of such response curves is shown in FIG. 4. In general, the slope of the capacitance versus relative humidity curve for each capacitor becomes steeper the higher the initial capacitance of the sensor. The response is uniformly linear, however, and this permits a response curve to be predicted from the measurement of capacitance versus relative humidity at only two points. This can be accomplished using known relative humidity standards. For example, a standard published the American Standard Society for Testing and Materials under designation E104-85 provides a method for creating known constant relative humidity by means of aqueous solutions. Certain saturated salt aqueous solutions provide standard relative humidity atmospheres in closed beakers at standard pressure and at varying temperatures from 0° C. to 100° C. For example, the equilibrium relative humidity of lithium chloride in solution will vary from 11.23% relative humidity at 0° C. to 9.90% relative humidity at 100° C. Similarly potassium chloride varies from 88.61% relative humidity (0° C.) to 78.50% relative humidity at 100° C. Thus, this methodology provides relative humidity standards which may be used to calibrate relative humidity sensing capacitors before they are placed into a sensor unit and installed in the field. By measuring the capacitance of a capacitor at two known relative humidities, a memory map may be constructed which provides a response curve representing the actual performance of the capacitor at two known relative humidity points. This information can then be stored in a memory in the sensor unit just before the unit is installed in the field, and can be subsequently used to calibrate the measurements made by the sensor unit, thus compensating for possible changes in capacitance as a result of shipping, handling and aging.

Referring to FIG. 2 the sensor electronics 18 are shown in more detail. The sensor capacitor 16 is a feedback capacitor in an integrator amplifier U1B. The output of U1B is coupled to an input of comparator amplifier U1A. The other input to U1A comes from switch $S_Z$ which is controlled by electronic switch 22. The electronic switch 22 also controls switch $S_Y$. A power supply 24 develops a voltage V1 through resistor R1 which is input to a voltage divider network 28 consisting of identical resistors R2 and R3. A voltage V2 is present at a center tap 26 in the voltage divider network 28 and a voltage V3 is present at the output end of the voltage divider network 28. The center tap 26 of the voltage divider network 28 is coupled to the other input of integrating amplifier U1B. A nonvolatile memory 20 stores calibration data for the sensing capacitor 16 in the manner described above.

The negative input to amplifier U1B depends on the state of switch $S_Y$. Similarly the input to comparator amplifier U1A depends on the state of switch SZ. Both switches $S_Y$ and $S_Z$ are controlled by switch controller 22. Switch controller 22 is in turn controlled by the output of U1A. Switches $S_Y$ and $S_Z$ alternately toggle between the input and output points of the voltage divider 28. In FIG. 2 the position of the switches is such that V3, the output of the voltage divider 28, is provided through R5 to the negative input of U1B while V1 at the input to the voltage divider is provided through switch $S_Z$ to the negative input of U1A. When the output of U1A changes state the switch controller 22 toggles the switches so that voltage V1 is coupled through R5 and voltage V3 is present at the input to U1A. Referring to FIG. 3 the output of U1B which is shown in the upper curve is a sawtooth waveform that toggles between V1 and V3. The output of U1A is a square wave of the same frequency that provides an output to the data processing unit 14. The frequency of the output of U1B is determined by the capacitance of sensor 16 which is in turn determined by the relative humidity.

The voltage divider network 28 makes the circuit of the sensor unit 12 independent of variations in temperature. To the extent that temperature causes a change in the output of the power supply 24 or changes any of the nominal component values, these changes are compensated for by the voltage divider network 28 and the switching arrangement provided by switches $S_Y$ and $S_Z$. This is because resistors R2 and R3 are identical and any change in the bias level at amplifier U1B is offset by a corresponding change in the threshold level at amplifier U1A. Thus, despite changes in temperature causing component value changes, the frequency of the output waveform is unaffected and is determined only by the relative humidity.

The output of sensor electronics 18 and memory device 20 are provided to a microprocessor 24. The microprocessor 24 has a memory unit 26 which stores the data from memory unit 20. The data in memory unit 26 is used to correct the relative humidity data provided by the sensor 16 in accordance with the algorithm used by the microprocessor 24. Since the output of the sensor electronics 18 is a square wave representing frequency, the microprocessor 24 employs a counter to derive a number representing the frequency of the oscillator formed by the switch 22 and the amplifiers U1A and U1B. Similarly, the other data representing relative humidity is converted to a frequency count. The algorithm thus used by the microprocessor is:

(calibrated zero RH count−sensor Count)/(High RH count−Low RH count)×4,096

This calculation provides a corrected relative humidity reading. The calibrated zero RH number is the sensor capacitance at zero relative humidity. The "sensor count" is the number provided by the sensor 16. The calibrated high relative humidity number and the calibrated low relative humidity number are the data points stored in memory as a result of measurements of the capacitor 16 made using the known standard relative humidity solutions referred to above. The number 4,096 is a conversion factor that converts from a frequency count number to a relative humidity in percent.

Figure 5:
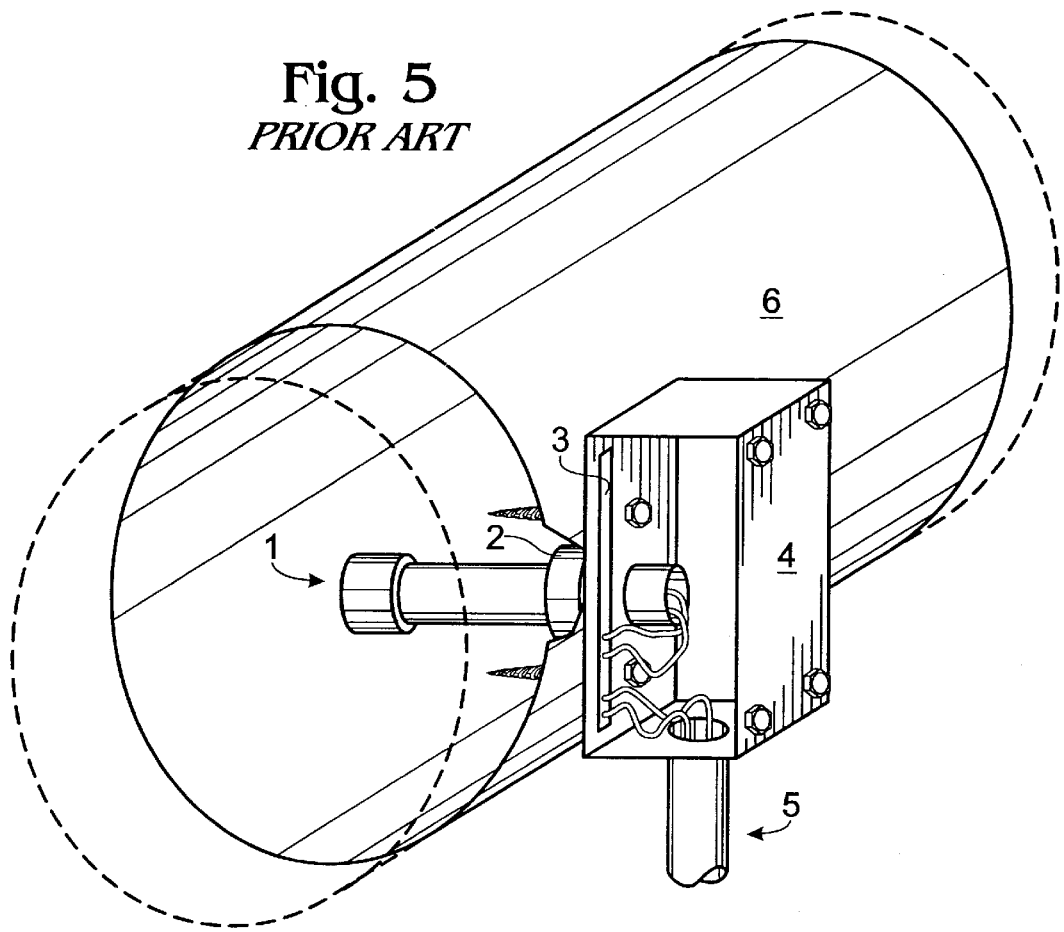
FIG. 5 is a partial cutaway perspective view of a prior art mounting for a relative humidity sensor.

In older units (FIG. 5), the humidity sensor 1 was mounted on the end of the tube which was secured through a duct 2 to a conduit box 4 containing a circuit board 3 which housed sensor electronics. This made replacement of the sensor units extremely cumbersome because it was be necessary to either enter the duct 6 or dismantle the conduit box 4 and the conduit pipe 5 from the duct 6.

For convenience, the sensor unit and the data processing unit may be packaged together in a tube 40 which is inserted through an aperture 42 in a duct or wall 44. Inside the duct or wall 44 is an environment in which relative humidity is to be measured. A mounting enclosure 46 is secured to the duct or wall 44 by bolts 48 and has a corresponding aperture 50 aligned with the aperture 42. A sleeve 52 projects from the mounting enclosure 46 through the duct aperture 42. On the inside of the mounting enclosure 46 the sleeve 52 includes exterior threading which is engageable by a swage nut 54. The swage nut 54 tightens down against the tube 40 to hold it in place within the apertures 42 and 50. The tube 40, therefore, extends securely into the environment enclosed within the duct 44. The humidity sensitive element 16 is mounted at the end of the tube 40.

This physical arrangement permits user to easily replace either the sensor or sensor electronics by simply unscrewing the swage nut and pulling the tube 40 from the mounting enclosure 46.

Figure 6:
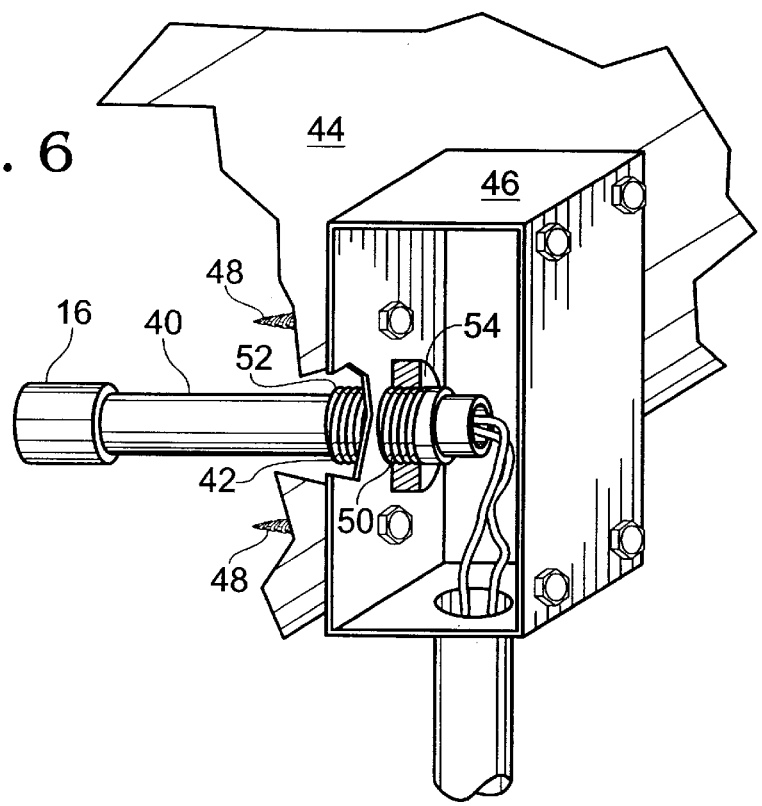
FIG. 6 is a partial cutaway perspective view of the mounting system for the relative humidity sensor of the invention.

Although the preferred embodiment shown in FIG. 6 employs a swage nut tightening upon a sleeve to hold the tubular probe in place, other methods of securing the tube may be employed. Such well known equivalents as clamps, pins or other friction imparting devices may be used if desired to secure the tubular probe.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A humidity sensing device for insertion into an environment to be measured through a wall or duct comprising:

(a) a tubular housing;
   (b) an electronic circuit mounted in said housing, said circuit including a humidity sensing element, said element being mounted at an end of said tubular housing;
   (c) a mounting enclosure secured to said wall or duct and including an aperture aligned with an aperture in said wall or duct and dimensioned to accommodate said tubular housing; and
   (d) a releasably detachable securing fastener that secures said tubular housing to said enclosure and within said apertures so as to extend said housing into said environment and for allowing movement of said tubular housing relative to said enclosure when said securing structure is released.

2. The humidity sensing device of claim 1 wherein said securing means comprises an exteriorly threaded sleeve member and a swage nut for tightening said sleeve member onto said tubular housing.

3. The humidity sensing device of claim 1 wherein said tubular housing is a cylinder.

4. The humidity sensing device of claim 1 wherein said enclosure is secured to said wall or duct independently of said detachable securing fastener.

5. The humidity sensing device of claim 1 wherein said enclosure has a sleeve projecting through said aperture in said wall or duct and said tubular housing fits within said sleeve.

6. The humidity sensing device of claim 1 wherein said detachable securing fastener is located within said enclosure.

7. The humidity sensing device of claim 1 wherein said humidity sensing element is detachable from said tubular housing when said detachable securing fastener is released.

* * * * *

UNITED STATES PATENT AND TRADEMARK OFFICE
CERTIFICATE OF CORRECTION

PATENT NO. : 5,922,939
DATED : July 13, 1999
INVENTOR(S) : Roger Cota

It is certified that error appears in the above-identified patent and that said Letters Patent is hereby corrected as shown below:

Column 4,
Line 23, change "SZ" to -- $S_Z$ --.

Column 5,
Line 18, change "was be necessary" to -- was necessary --.

Signed and Sealed this

Thirteenth Day of December, 2005

JON W. DUDAS
*Director of the United States Patent and Trademark Office*